(12) United States Patent
Mulye et al.

(10) Patent No.: US 6,416,786 B1
(45) Date of Patent: Jul. 9, 2002

(54) SUSTAINED RELEASE TABLET CONTAINING HYDROCOLLOID AND CELLULOSE ETHER

(75) Inventors: Nirmal Mulye, Long Beach, NY (US); Kavita Inamdar, Mumbai (IN)

(73) Assignee: Nostrum Pharmaceuticals, Inc., Long Beach, NY (US)

( * ) Notice: Subject to any disclaimer, the term of this patent is extended or adjusted under 35 U.S.C. 154(b) by 0 days.

(21) Appl. No.: 09/459,300

(22) Filed: Dec. 10, 1999

Related U.S. Application Data
(60) Provisional application No. 60/111,964, filed on Dec. 11, 1998.

(51) Int. Cl.[7] .................................................. A61K 9/22
(52) U.S. Cl. ........................ 424/468; 424/464; 424/465; 424/485
(58) Field of Search ................................ 424/485, 468, 424/458, 465

(56) References Cited

U.S. PATENT DOCUMENTS

| | | |
|---|---|---|
| 4,369,172 A | 1/1983 | Schor et al. |
| B14,389,393 A | 10/1985 | Schor et al. |
| 4,610,870 A | 9/1986 | Jain et al. |
| 4,695,467 A | 9/1987 | Uemura et al. |
| 4,704,285 A | 11/1987 | Alderman |
| 4,734,285 A | 3/1988 | Alderman |
| 4,752,479 A | 6/1988 | Briggs et al. |
| 4,775,535 A | 10/1988 | Lowey |
| 4,786,518 A | 11/1988 | Nakel et al. |
| 4,792,452 A | 12/1988 | Howard et al. |
| 4,795,327 A | 1/1989 | Gaylord et al. |
| 4,832,956 A | 5/1989 | Gergely et al. |
| 4,855,143 A | 8/1989 | Lowey |
| 4,880,830 A | 11/1989 | Rhodes |
| 4,882,169 A | 11/1989 | Ventouras |
| 4,966,768 A | 10/1990 | Michelucci et al. |
| 4,973,470 A | 11/1990 | Mills et al. |
| 4,994,276 A | 2/1991 | Baichwal et al. |
| 5,002,774 A | 3/1991 | Agrawala et al. |
| 5,006,346 A | 4/1991 | Edgren et al. |
| 5,047,248 A * | 9/1991 | Calanchi et al. ............ 424/485 |
| 5,063,205 A | 11/1991 | Peters et al. |
| 5,077,051 A | 12/1991 | Gallopo et al. |
| 5,126,145 A | 6/1992 | Evenstad et al. |
| 5,128,143 A | 7/1992 | Baichwal et al. |
| 5,135,757 A | 8/1992 | Baichwal et al. |
| 5,143,732 A | 9/1992 | Helbig et al. |
| 5,169,639 A * | 12/1992 | Baichwal et al. ............ 424/468 |

(List continued on next page.)

OTHER PUBLICATIONS
PCT International Search Report dated Apr. 18, 2000.

Primary Examiner—Thurman K. Page
Assistant Examiner—Liliana Di Nola-Baron
(74) Attorney, Agent, or Firm—Scully, Scott, Murphy & Presser

(57) ABSTRACT

The present invention is directed to a solid sustained release pharmaceutical tablet for administering to a host, comprising a therapeutically effective amount of a pharmaceutically active ingredient and a sustained release carrier therefor, said sustained release carrier comprising (a) a hydrocolloid selected from the group consisting of xanthan gum, guar gum, and alginic acid or a pharmaceutically acceptable salt thereof, and (b) a cellulose ether, said hydrocolloid and cellulose ether being present in synergistic effective amounts to retard release of said pharmaceutically active ingredient, said hydrocolloid being present in amount ranging from about 0.3% to about 7.0% by weight of the tablet and said cellulose ether being present in an amount ranging from 3% to about 20% of said tablet, and said cellulose ether being present in said carrier in amounts equal to or greater than 33% by weight and said carrier being present in amounts less than 35% by weight of said tablet.

47 Claims, 3 Drawing Sheets

U.S. PATENT DOCUMENTS

| | | |
|---|---|---|
| 5,223,268 A | 6/1993 | Stetsko et al. |
| 5,292,534 A | 3/1994 | Valentine et al. |
| 5,338,550 A | 8/1994 | Edgren et al. |
| 5,372,998 A | 12/1994 | Kokubo et al. |
| 5,415,871 A | 5/1995 | Pankhania et al. |
| 5,419,917 A | 5/1995 | Baichwal |
| 5,427,799 A | 6/1995 | Valentine et al. |
| 5,455,046 A | 10/1995 | Baichwal et al. |
| 5,464,633 A | 11/1995 | Conte et al. |
| 5,472,711 A | 12/1995 | Baichwal et al. |
| 5,478,574 A | 12/1995 | Baichwal et al. |
| 5,512,297 A | 4/1996 | Baichwal et al. |
| 5,543,155 A | 8/1996 | Fekete et al. |
| 5,554,387 A | 9/1996 | Baichwal et al. |
| 5,582,837 A | 12/1996 | Shell |
| 5,612,053 A | 3/1997 | Baichwal et al. |
| 5,662,933 A | 9/1997 | Baichwal et al. |
| 5,667,801 A | 9/1997 | Baichwal |
| 5,670,168 A | 9/1997 | Baichwal et al. |
| 5,681,583 A | 10/1997 | Conte et al. |
| 5,700,832 A | 12/1997 | Baik et al. |
| 5,738,865 A | 4/1998 | Baichwal et al. |
| 5,741,519 A | 4/1998 | Rosenberg et al. |
| 5,741,524 A | 4/1998 | Staniforth et al. |
| 5,773,025 A | 6/1998 | Baichwal |
| 5,780,057 A | 7/1998 | Conte et al. |
| 5,804,217 A | 9/1998 | Bjork et al. |
| 5,811,126 A | 9/1998 | Krishnamurthy |
| 5,846,563 A | 12/1998 | Baichwal |
| 5,851,555 A | 12/1998 | Sanghvi et al. |
| 5,858,412 A | 1/1999 | Staniforth et al. |
| 5,876,752 A | 3/1999 | Herbig et al. |
| 5,885,615 A | 3/1999 | Chouinard et al. |
| 5,895,663 A | 4/1999 | Irwin et al. |

* cited by examiner

SUSTAINED RELEASE TABLET CONTAINING HYDROCOLLOID AND CELLULOSE ETHER

RELATED APPLICATIONS

The present application is claiming benefit of the provisional application, U.S. Ser. No. 60/111,964 filed on Dec. 11, 1998.

FIELD OF THE INVENTION

This invention relates to a controlled release formulation of a therapeutic agent and in particular to a sustained release formulation, in which the carrier comprises a synergistic effective amount of a hydrocolloid and cellulose ether.

BACKGROUND OF THE INVENTION

Sustained or slow release compositions containing pharmaceutical medicaments or other active ingredients are designed to contain higher concentrations of the medicament and are prepared in such a manner as to effect sustained or slow release into the gastro-intestinal digestive tract of humans or animals over an extended period of time. Well absorbed oral sustained or slow release therapeutic drug dosage forms have inherent advantages over conventional, immediate release dosage forms. The advantages include less frequent dosing of a medicament and resultant patient regime compliance, a more sustained drug blood level response, the possibility of effecting therapeutic action with less ingested drug and the mitigation of side effects. By providing a slow and steady release of the medicament over time, absorbed drug concentration spikes are mitigated or eliminated by effecting a smoother and more sustained blood level response.

For this purpose a retard formulation has to meet some criteria, namely causing an uniform and constant dissolution and being effective for an extended period of time. It is also important that such a formulation be simple to make and that the manufacturing process be reproducible and be used for a number of different substances.

To prepare sustained release formulations in the form of a solid oral dosage, such as tablets, various hydrophilic polymers have been utilized.

For example, hydroxypropylmethyl cellulose has been used as a polymer for controlled release formulation. For instance, U.S. Pat. Nos. 4,259,341 to Lowey, U.S. Pat. No. 3,870,190 to Lowey, et al., U.S. Pat. No. 4,226,849 to Schor, and U.S. Pat. No. 4,357,469 to Schor relate to the preparation of tablets having a hydrophilic matrix comprised of hydroxypropylmethyl cellulose alone or mixed with other cellulose derivatives. In addition, U.S. Pat. Nos. 4,369,172 and 4,389,393 to Schor, et al. relate to a sustained release formulation in which the carrier associated therewith contains hydroxypropylmethyl cellulose alone or mixed with methyl cellulose and or sodium carboxy methyl cellulose. Sheth in U.S. Pat. Nos. 4,167,448 and 4,126,672 relate to the use of a pharmaceutical composition containing hydroxypropylmethyl cellulose.

Another polymer that has been used in controlled release formulations is xanthan gum.

U.S. Pat. Nos. 5,292,534 and 5,427,799 to Valentine, et al. disclose a sustained release formulation comprising a pharmaceutical e.g., niacin with xanthan gum wherein the xanthan gum is present in 20–50 wt %. of the formulation.

U.S. Pat. No. 5,415,871 to Pankhania, et al. is directed to a sustained release pharmaceutical formulation comprising xanthan gum, a pharmaceutically active ingredient, for example, ibuprofen or flurbiprofen and other optional excipients. In this formulation, the carrier which consists essentially of the xanthan gum is at least 50% xanthan gum by weight. U.S. Pat. No. 5,047,248 to Calanchi also discloses a pharmaceutical composition consisting of a pharmaceutically active substance and 10–80 weight percent of a matrix, in which the matrix consists of 31–100% xanthan gum. Although Calanchi, et al. suggest combining xanthan gum with other natural or synthetic polymers, such as polymers which hydrate and dissolve in water, e.g., methyl cellulose, hydroxyethyl cellulose, or polymers having pH dependent solubility, or polymers hydrating and dissolving slowly in water, such as hydroxypropylmethyl cellulose; however, no one heretofore not, even Calanchi, et al. contemplate or suggest that in certain concentrations the xanthan gum and the hydroxypropylmethyl cellulose exhibit a synergistic effect, thereby forming a pharmaceutical carrier have significantly improved sustained release properties. This is an aspect of the present invention which the present inventors have found.

Moreover, the present invention fulfills an important need in the pharmaceutical arts. When cellulose ethers as well as hydrocolloids are used as carriers in controlled release formulations, they are usually present in high concentrations and they are a major constituent of the tablet. Unfortunately, high polymer content can adversely affect the tableting properties when prepared as dry blends and can cause difficulties when the wet granulation technique is used to form granules. Ideally, many of these problem would be alleviated if the sustained release carrier were present in lower concentrations, as this would allow the tablet size to remain small, permit it to be manageable for ingestion as well as allow addition of excipient thereto which improves compressibility thereof. Moreover, a low concentration of a sustained release carrier would enhance the ability to formulate drugs in compositions wherein the drug is present in high doses, e.g., in excess of 500 mg per tablet. The present invention by combining a hydrocolloid with a cellulose ether achieves this objective.

For a sustained release carrier to function well, the cellulose ether or hydrocolloid therein must hydrate quickly when it comes in contact with water to form a gel and control the release of the drug. However, the gel that is formed must be firm to prevent fast dissolution or erosion of the protective gel. Unfortunately, many polymers of cellulose ether, including various form of hydroxypropylmethyl cellulose, form firm gels but do not hydrate quickly enough to be useful as carrier. To date, only the Methocel K version of hydroxypropylmethyl cellulose has been used as a carrier in many pharmaceutical compositions, but in many cases, high concentrations thereof must be used. On the other hand, hydrocolloids, such as xanthan gum, are hydrophilic and thus hydrate very quickly. But they cannot form a strong gel, causing erosion or dissolution of gel around the tablet, thereby requiring high concentrations of such polymers to control the release. The present inventors have found, however that a synergistic combination of hydrocolloids and cellulose ether overcomes this problem, and permits the formulator to tailor the release profile for a particular drug.

SUMMARY OF THE INVENTION

Accordingly, the present invention is directed to a sustained release pharmaceutical tablet for administering to a host, said tablet comprising a pharmaceutically effective amount of an active ingredient, and a sustained release carrier, said carrier comprising a hydrocolloid selected from the group consisting of xanthan gum, guar gum and alginic acid or a pharmaceutically acceptable salt thereof and (b) a cellulose ether, said hydrocolloid and cellulose ether being present in a synergistic effective amount sufficient to retard the release of said pharmaceutically active ingredient, said carrier being present in less than about 40% by weight of said tablet, said hydrocolloid being present in an amount ranging from 0.3% to about 7.0% of said tablet, and said cellulose ether being present in an amount ranging from 3% to about 25% by weight of the tablet, with said cellulose ether being present in at least about 33% by weight of the carrier.

DETAILED DESCRIPTION OF THE INVENTION

Figure 1:
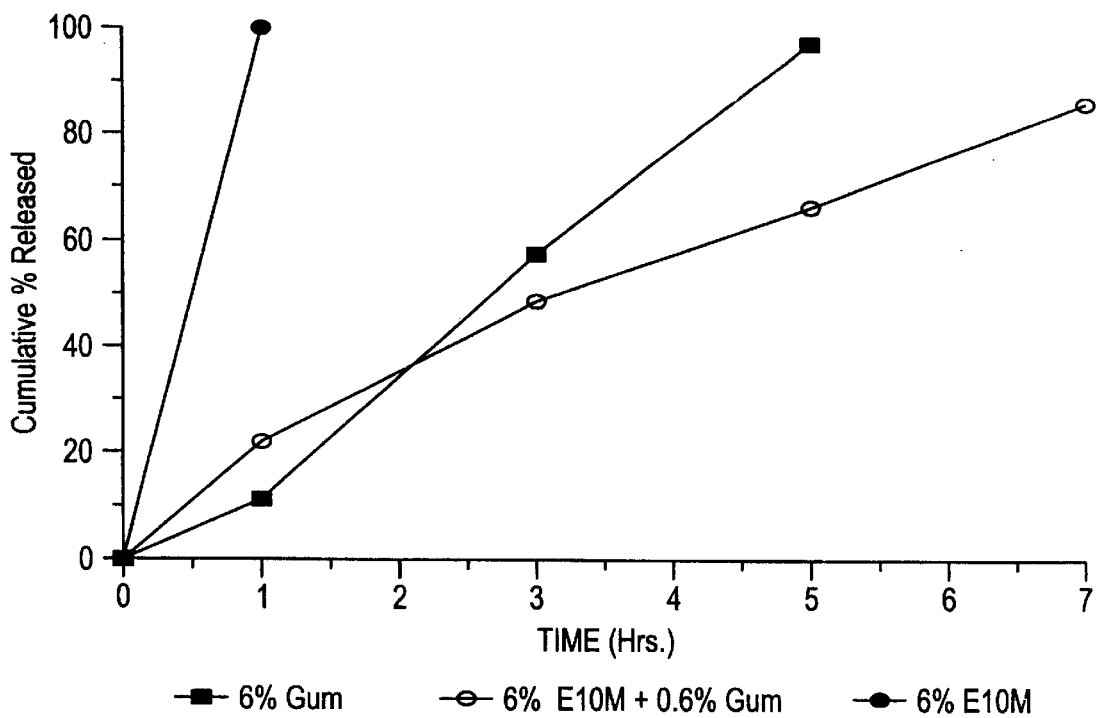
FIG. 1 shows a release profile of guaifenesin in water when the carrier is xanthan gum, hydroxypropylmethyl cellulose and a combination thereof in synergistic amounts.

The present invention is directed to a sustained release formulation of a pharmaceutically active ingredient in which the pharmaceutical carrier associated therewith comprises cellulose ether polymer and a hydrocolloid present in synergetic effective amounts, as defined herein.

The percent of the ingredient required in the formulation of the present invention, e.g., the active ingredient, the hydrocolloid, the lubricant and other ingredients are calculated on a dry weight basis without reference to any water or other component present.

By "sustained release" it is meant for purposes of the present invention that the therapeutically active medicament or drug is released from the formulation at a controlled rate such that therapeutically beneficial blood levels (but below toxic levels) of the medicament are maintained over an extended period of time, e.g., providing 4, 8, 12, 16, or 24 hours dosage form.

The present formulation comprises a pharmaceutical composition in unit dosage form. The term "unit dosage form", as employed herein, refers to a physically discrete unit suitable as unitary dosage to mammals, including humans, with each unit containing a predetermined quantity of active material calculated to produce the desired effect in association with the carrier, the lubricant and other ingredients of the formulation as described herein.

The present formulation is applicable to a wide variety of drugs or active medicaments suitable for use in sustained release formulations.

Representative active medicaments include antacids, anti-inflammatory substances, coronary vasodilators, cerebral vasodilators, psychotropics, antimanics, stimulants, antihistamines, laxatives, decongestants, vitamins, gastrointestinal sedatives, anti-diarrheal preparations, antianginal drugs, vasodilators anti-arrythmics, anti-hypertensive drugs, vasoconstrictors and migraine treatments, anti-coagulants and anti-thrombotic drugs, analgesics, anti-pyretics, hypnotics, sedatives, anti-emetics, anti-nauseants, anticonvulsants, neuromuscular drugs, hyper- and hypoglycemic agents, thyroid and anti-thyroid preparations, diuretics anti-spasmodics, uterine relaxants, mineral and nutritional additives, anti-obesity drugs, anabolic drugs, erythropoietic drugs, anti-asthmatics, expectorants, cough suppressants, mucolytics, anti-uricemic drugs and other drugs or substances acting locally in the mouth, such as topical analgesics, local anaesthetics, or combination thereof and the like. The present formulation may contain more than one active ingredient.

Among the possible drugs, the following are cited as illustrative and non-limiting: Niacin, guaifenesin, pseudoephedrine, phenylpropanolamine, dextromethorphan, diclofenac or salts thereof, isosorbide mononitrate, felodipine, metoprolol succinate, levodopa, carbidopa, glipazide and naproxen, and the like.

The medicaments are present in pharmaceutically effective amounts. It is preferred that the medicament be present in amounts ranging from about 0.5% to about 90% by weight of the tablet.

The pharmaceutical carrier of the present invention is comprised of the cellulose ether and the hydrocolloid in the prescribed quantities.

The cellulose ethers for use in this invention are hydrophilic polymers which are commercially available. Examples of cellulose ethers to be added to tablets of the present invention include carboxymethyl cellulose, methyl cellulose, hydroxyethyl cellulose, hydroxypropyl cellulose, hydroxybutyl cellulose, hydroxyethylmethyl cellulose, hydroxyethylethyl cellulose, hydroxypropylmethyl cellulose, hydroxypropylethyl cellulose, hydroxybutylmethyl cellulose, hydroxybutylethyl cellulose, carboxymethyl cellulose and salts thereof.

Moreover, the present invention includes the use of hydroxypropylmethyl cellulose in its various forms.

Hydroxypropylmethyl cellulose is commercially available in various grades, under several tradenames, including METHOCEL, E, F, J and K from The Dow Chemical Co., USA, HPM from British Celanese Ltd. England and Metaluse SH from Shin Etsu, Ltd, Japan. The various grades available under a given tradename represent differences in methoxyl and hydroxypropoxyl content as well as molecular weight. The methoxyl content ranges from 16.5 to 30 weight % and the hydroxypropoxyl content ranges from 0 to 32 weight -%, as determined by the method described in ASTM D-2363-72. All of these various forms of hydroxypropylmethyl cellulose are contemplated to be used in the present invention. For example, the present invention contemplates the use of Methocel K in its various forms having a methoxyl content of 19–24% and a hydroxypropoxyl content of 7–12%, Methocel E in its various forms, having a methoxyl content of 28–30 to and a hydroxypropyl content of 7–12%, Methocel F in its various forms having a methoxyl content of 27–30% and a hydroxypropoxyl content of 4–7.5%, Methocel A in its various forms, having a methoxyl content of 27.5–31.5% and about 0% hydroxypropoxyl content.

Commercial designations of the various hydroxypropylmethyl cellulose are based on the viscosities of 2% aqueous solutions at 20° C. The viscosities range from 15 cps to 30,000 cps and represent number average molecular weights ranging from about 10,000 to over 150,000, as calculated from the data in the "Handbook of Methocel Cellulose Ether Products" (The Dow Chemical Co., 1974).

Examples of hydroxypropylmethyl cellulose include Metalose 60 5H50 which is a hydroxypropylmethyl cellulose having a hydroxypropoxyl content of 9–12 weight % and a number average molecular weight of less than 50,000; Methocel E4M, having a 28–30 weight % methoxyl content, a viscosity of 4000 cps, a hydroxy-propoxyl weight % of 7–12 and a number average molecular weight of 93,000; Methocel E10M, having a viscosity of 10,000 cps, a 28–30 weight % methoxyl content, 7–12 weight % hydroxypropoxyl, Methocel K4M, having a number average molecular weight of 89,000, viscosity of 4,000, 19–24% weight % methoxyl content, and a 7–12 weight % hydroxypropoxyl content; Methocel K15M, having a number average molecular weight of 124,000, a 19–24 weight % methoxyl content and a 7–12 weight % hydroxypropoxyl content; and K100M, having a viscosity of 100,000 cps and a 19–24 weight % methoxyl content and is 7–12 weight % hydroxypropoxyl content, Methocel J5M, J12M, J20M and J75M, having viscosities of 5,000, 12,000, 20,000, and 75,000, cps, respectively and the like. Various hydroxypropylmethyl cellulose materials which can also be used in the present formulation are described in U.S. Pat. No. 3,870,790 to Schorr, U.S. Pat. No. 4,226,849 to Schorr, U.S. Pat. No. 4,357,469 to Schorr, U.S. Pat. No. 4,369,172 to Schorr, et al., U.S. Pat. No. 4,389,393 to Schorr, et al., U.S. Pat. No. 4,259,314 to Lowey, U.S. Pat. No. 4,540,566 to Davis, et al., U.S. Pat. No. 4,556,678 to Hsiau, the contents of all of which are incorporated herein by reference. The present formulation may contain one cellulose ether or a combination of cellulose ethers.

The other essential ingredient of the carrier is the hydrocolloid. They are hydrophilic polymers, i.e., soluble in water. The present invention does not contemplate the use of any hydrocolloid, only certain hydrocolloids are useful in the present invention. These are guar gum, alginic acid and its pharmaceutically acceptable salts e.g., sodium alginate and xanthan gum. The present formulation may contain one hydrocolloid or a combination of hydrocolloids.

The preferred hydrocolloid is xanthan gum. Xanthan gum is a high molecular natural carbohydrate and more particularly polysaccharide produced by the fermentation process of the microorganism Xanthomonas campetris. The molecular weight of the xanthan gum polymer is probably on the order of 2 million, but has reported to be as high as 13–50 million. These reported differences are most probably due to association phenomena between the polymer chains. The xanthan gum used in the present invention is preferably in a dry, free, flowing granular or powdered form, with a preferred average particle size ranging between 850–74 microns.

The hydrocolloid and the cellulose ethers are present in synergistic effective amounts. As defined herein, and explained in more detail hereinbelow, when the cellulose ether and the hydrocolloid of the present invention are present in prescribed amounts, the sustained release ability exhibited by the tablet is more than just an additive effect. More specifically, the present formulation exhibits a better drug release profile when the carrier comprises the hydrocolloid and cellulose ether in the prescribed amounts, than either one by themselves. In another embodiment, the present formulation may exhibit a slower drug release than the formulation containing only one of the components, hydrocolloid or cellulose ether alone. Alternatively, if either the hydrocolloid or cellulose ether exhibit an excellent drug release profile, the formulation of the present invention also exhibits the same or substantially the same drug profile but utilizing a smaller amount of cellulose ether and hydrocolloid in total. As used herein, the term synergistic effective amounts is the amount of xanthan gum and hydrocolloid in combination to effect any one of these or other improved result in the present formulation relative to a formulation containing only one or the other. The carrier is preferably comprised of at least 33% by weight cellulose ether and more preferably greater than about 50% cellulose ether, and even more preferably greater than about 60% and even more preferably greater than about 66% and even more preferably greater than about 75% by weight cellulose ether. Furthermore, in a preferred embodiment, the present tablet is comprised of about 3% to about 25% by weight cellulose ether and more preferably from about 3 to about 15% by weight.

The hydrocolloid is present in amounts ranging from about 0.3% to about 10% by weight and more preferably from about 1% to about 5% by weight of the tablet. It is present in 66% or less in the carrier by weight and more preferably from about 5% to about 40% by weight, and most preferably from 10% to about 33% by weight of the carrier.

As defined herein the hydrocolloid and the cellulose ether comprise the pharmaceutical carrier associated with the drug. It is preferred that the pharmaceutical carrier be at most about 40% by weight of the tablet, and more preferably be at most 35% by weight of the tablet and most preferably at most about 30% by weight of the tablet. Preferably, the carrier is present in amounts ranging from about 3% to about 25% and most preferably from about 6% to about 20% by weight of the tablet.

Moreover, it is preferred that the cellulose ether and hydrocolloid be present in weight ratio in a prescribed range, preferably from about 1:0.01 to about 1:2, and more preferably from 1:0.05 to about 1:0.4.

The cellulose ethers and hydrocolloids used in the present invention are commercially available.

The present formulation also contains optional components. For example, although not necessary, in a preferred embodiment, the present formulation additionally contains a lubricant that is typically used in the pharmaceutical arts for oral tablets. As used herein, the term "lubricant" refers to a material which can reduce the friction between the die walls and the punch faces which occurs during the compression and ejection of a tablet. The lubricant prevents sticking of the tablet material to the punch faces and the die walls. As used herein, the term "lubricant" includes anti-adherents. Examples of lubricants include stearate salts, e.g., alkaline earth, and transition metal salts thereof, e.g., calcium, magnesium, or zinc; stearic acid, polyethylene oxide, talc, hydrogenated vegetable oil, and vegetable oil derivatives, silica, silicones, high molecular weight polyalkylene glycol, e.g., high molecular weight polyethylene glycol, monoesters of propylene glycol, saturated fatty acid containing about 8–22 carbon atoms and preferably 16–20 carbon atoms. The preferred lubricants are the stearate salts, stearic acid, talc and the like.

To avoid tablet sticking during formation and or ejection, the present formulation contemplates utilizing a lubricating effective amount of the lubricant. Preferably, the lubricant is present in amounts ranging from about 0.1% to about 5% by weight and more preferably from about 1% to about 4% by weight of the tablet.

Another optional ingredient is an inert filler. The filler may substantially water soluble or water insoluble. A filler is used if need or desired although not necessary for the present formulation. The fillers used in the present formulation are those typically used in the pharmaceutical arts for oral tablets. Examples include calcium salts, such as calcium sulfate, dicalcium phosphate, tricalcium phosphate, calcium lactate, calcium gluconate, and the like, glycerol phosphate; citrates; and mixture thereof, and the like. However, the inert filler of the sustained release formulation of the present invention preferably comprises a pharmaceutically acceptable saccharide, including a monosaccharide, a disaccharide, or a polyhydric alcohol and/or mixtures of any of the foregoing. Examples thereof include sucrose, dextrose, lactose, microcrystalline cellulose, fructose, xylitol, sorbitol, mixtures thereof and the like. The filler, if present, is present in amounts ranging from about 1% to about 90% by weight.

Other optional ingredients that are also typically used in pharmaceuticals may also be present, such as coloring agents, preservatives (e.g., methyl parabeans), artificial sweeteners, flavorants, antioxidizing agents and the like. Artificial sweeteners include, but are not limited to saccharin sodium, aspartame, dipotassium glycyrrhizinate, stevia, thaumatin and the like. Flavorants include, but are not limited to lemon, lime, orange and menthol. The colorants include, but are not limited to various food colors, e.g., FD & C colors, such as FD & C Yellow No. 6, food lakes and the like. Examples of anti-oxidants include ascorbic acid, sodium metabisulphite, and the like. These optional ingredients, if present, are preferably present in amounts ranging from about 0.1% to about 5% by weight of the tablet and most preferably less than about 3% (w/w) of the tablet.

The present formulation of the present invention is prepared by blending the medicament with the lubricant, cellulose ether, hydrocolloid, and the other optional ingredients. The ingredients are mixed in a typical blender that is normally utilized in the pharmaceutical arts, such as a Hobart mixer, V-blender, a planetary mixer, Twin shell blender and the like. The ingredients are blended together typically at about ambient temperature; no additional heating is necessary, although slight modifications of temperature therefrom could be utilized. It is preferred that the blending be conducted at temperatures ranging from about 10° C. to about 45° C.

The ingredients in the formulation are preferably mixed together in a large batch using techniques well known in the pharmaceutical arts and are intimately intermixed until the mixture is homogenous with respect to the drug.

The term "homogenous" with respect to the drug is used to denote that the various components are substantially uniform throughout the invention, i.e., a substantially homogeneous blend is formed.

When the mixture is homogeneous, a unit dosage amount of the mixture is compressed into a tablet form using a tablet machine typically utilized in the pharmaceutical arts. More specifically, the mixture is fed to the die of a tablet press and sufficient pressure is applied to form a solid tablet. Such pressure can vary, and typically ranges from about 1,000 psi to about 6,000 psi and preferably about 2,000 psi force. The solid formulation according to the present invention is compressed to a sufficient hardness to prevent the premature ingress of the aqueous medium into the tablet. Preferably, the formulation is compressed into a tablet form which is of the order of 5–20 Kp and more preferably 8–20 Kp as determined by a Schleuniger hardness tested.

In a variation, all of the above steps are repeated, except that the mixing is initially performed in the absence of a lubricant. When the mixture is homogeneous with respect to the drug, then the lubricant is added and the mixing is continued until the lubricant is substantially evenly dispersed in the mixture. Then the mixing is terminated, and the mixture is immediately thereafter compressed into a tablet, as described hereinabove.

Another procedure for preparing the formulation of the present invention is by the wet granulation process in which all of the components except the lubricant are mixed with a sufficient amount of a granulating solvent to form a substantially uniform blend. The granulating vehicle is one that is inert with the components and has a low boiling point, i.e., preferably less than about 120° C. It is preferably a solvent that contains OH groups, such as an alcohol containing 1–4 carbon atoms, e.g., isopropyl alcohol or ethanol or water and the like. An aqueous dispersion can also be utilized. In a preferred embodiment, the type of granulating vehicle used is dependent upon the identity of the sustained release polymer. For example, it is preferred that when hydroxypropylmethyl cellulose is utilized, the granulating vehicle is water or alcohol.

The substantially uniformly blended mixture may optionally be milled, e.g., passed through a screen, sieve, etc. to reduce the size of the particles thereof. The screen or sieve, and the like is preferably less than about 140 mesh, and more preferably less than about 100 mesh, and even more preferably, less than about 40 mesh, and most preferably less than about 20 mesh.

Next, the blend is dried. In this step, the solvent is removed from the blend by physical means known to the skilled artisan, e.g., by evaporation. The resulting granules are again milled, e.g., passed through a screen or sieve to further reduce the size of the particles to the desired size. Then the lubricant is added, and the granules are mixed to provide a uniform blend, i.e., homogenous with respect to the drug and then the resulting mixture is compressed to form a tablet. In a preferred variation, the blend can be simultaneously granulated in the granulation vehicle and dried such as using a fluid bed granulation process.

After the tablet is formed, the tablet is coated with materials normally used in pharmaceuticals, if desired. If coated, the coating is prepared by techniques known in the art. However, the formulation of the present invention is preferably uncoated.

The tablet product is obtained which has the desired hardness and friability typically found for pharmaceutical tablets. The hardness is preferably 5–25 Kp and more preferably 8–20 Kp. The present formulation in tablet form has an excellent drug release profile. More specifically, it has a predetermined controlled and sustained action and a regular delayed pattern so that the medicament is available over a period of up to 36 hours, depending upon the precise tablet size, the identity of the active ingredient, aqueous solubility of the active ingredient, hardness and the particular carrier composition. For example, in accordance with the process of the present invention, a controlled release diet supplement can be prepared wherein the release time is 2–4 hours, 8 to 10 hours, 15–18 hours, 20–24 hours, etc. as desired. Furthermore, the release profile of each formulation is substantially uniform. Finally, the tablets prepared in accordance with the present invention are hard and dense, have low friability and provide controlled and sustained release over an extended period. Solid dry forms prepared by the present invention are stable and their release rate does not change to any significant (if any) extent over an extended period of storage.

The sustained release medicament is provided in solid form, conveniently in a unit dosage form. It is preferred to provide the sustained release medicament in solid unit dosage form for oral administration, especially in tablet form. Preferably, it is intended to release the pharmacologically active ingredient slowly or according to a prescribed rate after ingestion within the body as the formulation progresses along the gastro-intestinal tract. In this regard, the gastro-intestinal tract is considered to be the abdominal portion of the alimentary canal, i.e, the lower end of the esophagus, the stomach and the intestines.

The dosages of a formulation according to the invention correspond to the normal dosages of the particular active ingredient known to the skilled artisan. The precise amount of drug administered to a patient will depend on a number of factors, including the age of the patient, the severity of the condition and the past medical history, among other factors, and always lie within the sound discretion of the administering physician. For guideline as a suitable dosage, reference is made to the Physicians Desk Reference.

The presence of the synergistic effective amounts of the hydrocolloid in combination with the cellulose ethers provides an excellent drug release profile. When used in the amounts provided, the drug release profile is substantially better than the drug release profile using either the hydrocolloid or the cellulose alone in the same amounts. One aspect of the synergism is exemplified when the combination of the cellulose ether and, the hydrocolloid retard significantly better the release of the drug than either component alone. In another embodiment, especially when the concentration of cellulose ether is significantly greater than hydrocolloid, the present formulation surprisingly exhibit a drug profile similar not to the cellulose ether which is present in the greater amount, but rather more closely to the hydrocolloid, present in the smaller amount. Alternatively, the drug release profile of the present formulation wherein the hydrocolloid and the cellulose ether are present in synergistic effective amounts may be similar to the drug release profile of either component alone, but this is achieved using substantially less material of hydrocolloid and cellulose ether in total than when other component is used alone. These results leads to other advantages.

These include the use of smaller tablets which are more economical and are easy to administer. Moreover, high dosage drugs which normally result in large tablets can be prepared in smaller sustained-release dosage forms.

Moreover, it has been found that the combination of the cellulose ether and hydrocolloid in the synergistic amounts provided hereinabove give drug profile that may be obtained using a different sustained release polymer, but in those cases, the amounts of polymer used is considerably less.

Unless indicated to the contrary, all percentages are weight percentages relative to the tablet.

The following non-limiting examples further illustrate the present invention.

EXAMPLE 1

Niacin (1000 mg), xanthan gum (72 mg) METHOCEL E10M (hydroxypropylmethyl cellulose) (36 mg), silicified microcrystalline cellulose (80 mg) and Talc (12 mg) are thoroughly mixed in a blender for 120 minutes at room temperature. The above mixture is compressed using a tablet press.

EXAMPLE 2

Guaifenesin (600 mg), dextromethorphen hydro-bromide (31.5 mg), silicified microcrystalline cellulose (107.2 mg), METHOCEL E10M (74.7 mg), xanthan gum (8.3 mg), Talc (16.4 mg) and Aerosil (8.3 mg) were blended together on a V blender for 120 minutes at room temperature. Then the homogenous mixture was compressed to form a tablet.

EXAMPLE 3

Guaifenesin (600 mg), METHOCEL E10M (48 mg), xanthan gum (4.8 mg), silicified Microcrystalline cellulose (139.2 mg) and Talc (8 mg) were dry mixed on a V-blender for 120 minutes, and then compressed into a 800 mg tablet. The release profile thereof was determined with USP (U.S. Pharmacopoeia) apparatus (I or II) using water as the medium. The release profile is shown in FIG. 1.

COMPARATIVE EXAMPLE 1

Guaifenesin (600 mg), xanthan gum (48 ml), silicified MCC (144 mg) and Talc (8 mg) were mixed together. The formulation did not contain, however, any hydroxypropylmethyl cellulose. The mixture was compressed into a drug. The release profile was determined as in Example 3 and is shown in FIG. 1.

COMPARATIVE EXAMPLE 2

Guaifenesin (600 mg), METHOCEL E10M (48 mg), silicified MCC (144 mg) and Talc (8 mg) were mixed together. The formulation did not contain any xanthan gum. The mixture was compressed with a drug. The release profile was determined as in Example 3 and is shown in FIG. 1.

RESULTS

The release profile of the three formulations of Example 1 and Comparative Examples 1 and 2 are shown in FIG. 1. Example 3 contained 6% by weight METHOCEL E10M and 0.6% xanthan gum, while comparative Example 1 contained 6% by weight xanthan gum and comparative Example 2 contained 6% METHOCEL E4M. As clearly seen, the drug containing both the hydroxypropylcellulose and xanthan gum significantly retarded the release of the guaifenesin relative to the formulation when either the hydroxypropylmethyl cellulose or xanthan gum were present alone. More specifically, the formulation of the present invention was capable of releasing the drug more slowly.

EXAMPLE 4

Figure 2:
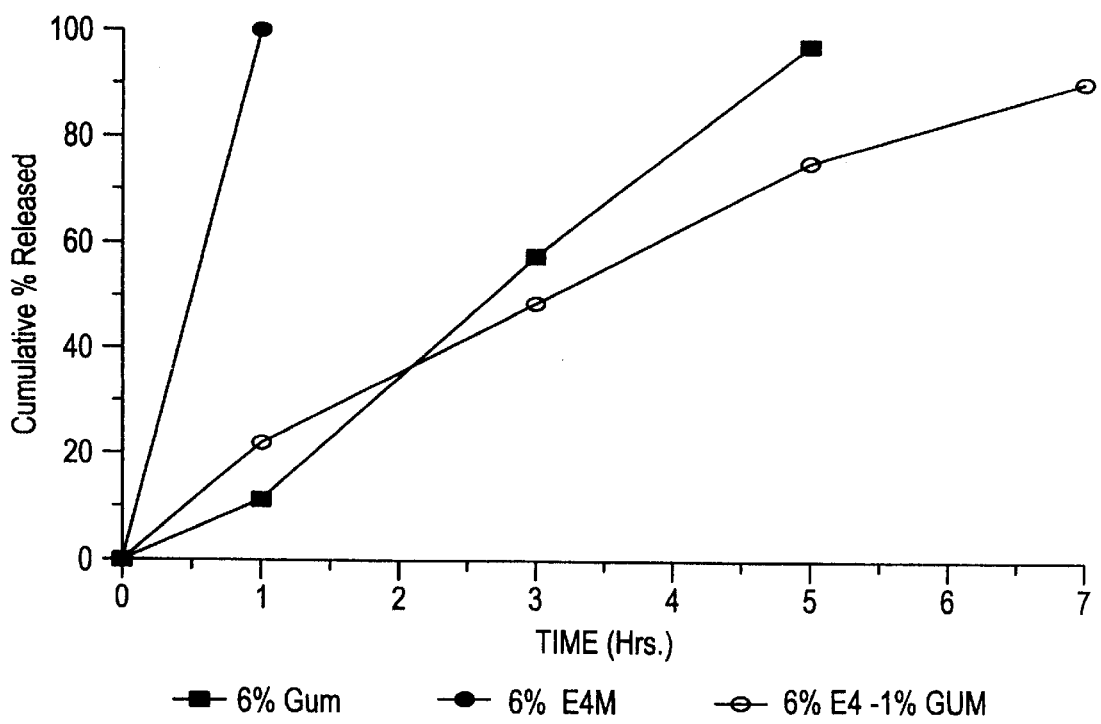
FIG. 2 shows a release profile of guaifenesin in water when the carrier is xanthan gum a different type of hydroxypropylmethyl cellulose than depicted in FIG. 1 and the combination thereof in synergistic effective amounts.

Guaifenesin (600 mg), METHOCEL E4M (48 mg), xanthan gum (8 mg), silicified microcrystalline cellulose (136 mg), and Talc (8 mg) were mixed together on a V blender for 120 minutes. The mixture was compressed into a 800 mg tablet. Its release profile was determined as in Example 3 and is depicted in FIG. 2.

COMPARATIVE EXAMPLE 3

Guaifenesin (600 mg), xanthan gum (48 mg), silicified microcrystalline cellulose (144 mg) and Talc (8 mg) were mixed together on a V blender for 120 minutes, in the absence of any hydroxypropylmethyl cellulose. The mixture was compressed into a 800 mg tablet. The release profile was determined as in Example 3 and is shown in FIG. 2.

COMPARATIVE EXAMPLE 4

Guaifenesin (600 mg), METHOCEL E4M CR (48 mg), silicified microcrystalline cellulose (144 mg) and Talc (8 mg) were mixed together as in Example 4. The mixture did not contain any xanthan gum. The mixture was compressed into a 800 mg tablet. The release profile was determined as in Example 3 and is shown in FIG. 2.

RESULTS

The release profile of the formulations of Example 4 and Comparative Examples 3 and 4 are shown in FIG. 2. Example 3 contained 6% METHOCEL 4 EM and 1% xanthan 9 gum by weight, while Comparative Example 3 contained 6% by weight xanthan gum and Comparative Example 4 contained 6% METHOCEL 4EM. As clearly shown, the drug formulation containing both the hydroxypropylmethyl cellulose and xanthan gum exhibited a better release profile than either of the formulations containing either the hydroxypropylmethyl cellulose or the xanthan gum. More specifically, the formulation of the present invention released the drug significantly more slowly.

EXAMPLES 5 & 6 AND COMPARATIVE EXAMPLES 5 & 6

800 mg tablets of guaifenesin were prepared as in Example 4, using the formulations tabulated herein below:

|  | 10% Gum | 10% E4M | 6% E4M + 1% Gum | 8% E4M + 1% Gum |
|---|---|---|---|---|
| Guaifenesin | 600 | 600 | 600 | 600 |
| Methocel E10M CR | 0 | 60 | 48 | 64 |
| Xanthan Gum | 60 | 0 | 8 | 8 |
| Silicified MCC | 132 | 132 | 136 | 124 |
| Talc | 8 | 8 | 8 | 8 |

Figure 3:
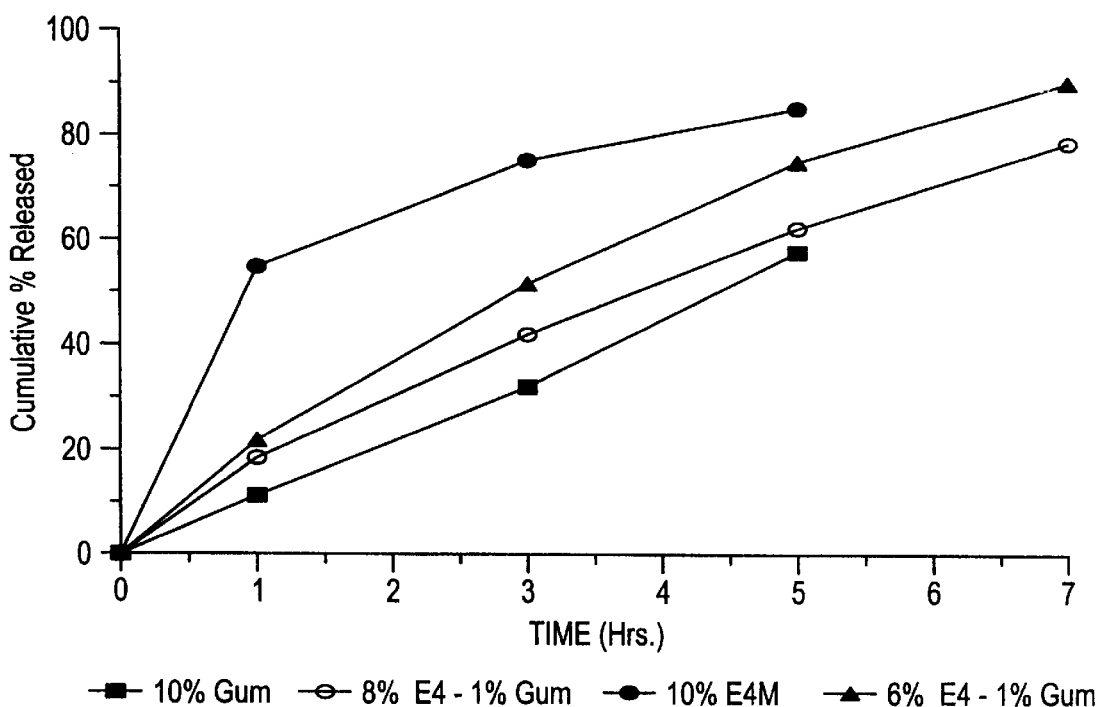
FIG. 3 shows a release profile of guaifenesin in water when the carrier is xanthan gum, hydroxypropylmethyl cellulose and a combination thereof in various concentrations in synergistic effective amounts.

The release profiles were determined as in Example 3 and are shown in FIG. 3. Although in the formulation of the present invention the hydroxypropyl methyl cellulose were present in significantly greater amounts than xanthan gum the release profile of this formulation was surprisingly more similar to that of the formulation containing the xanthan gum alone which had a slower drug release profile than that of the formulation containing the hydroxypropylmethyl cellulose alone.

EXAMPLE 7 & 8 AND COMPARATIVE EXAMPLES 7 & 8

800 mg tablets of guaifenesin were prepared as in Example 4 using the following formulation:

|  | 10% Gum | 12% E10M | 9% E10M + 3% Gum | 7% E10M + 7% LV |
|---|---|---|---|---|
| Guaifenesin | 600 | 600 | 600 | 600 |
| Methocel E10M CR | 0 | 96 | 72 | 56 |
| Xanthan Gum | 60 | 0 | 24 | 8 |
| Silicified MCC | 132 | 96 | 96 | 80 |
| Talc | 8 | 8 | 8 | 8 |
| HPMC K100 LV (Low Viscosity) |  |  |  | 56 |

*MCC = Microcrystalline cellulose
**HPMC = hydroxypropylmethyl cellulose

Figure 4:
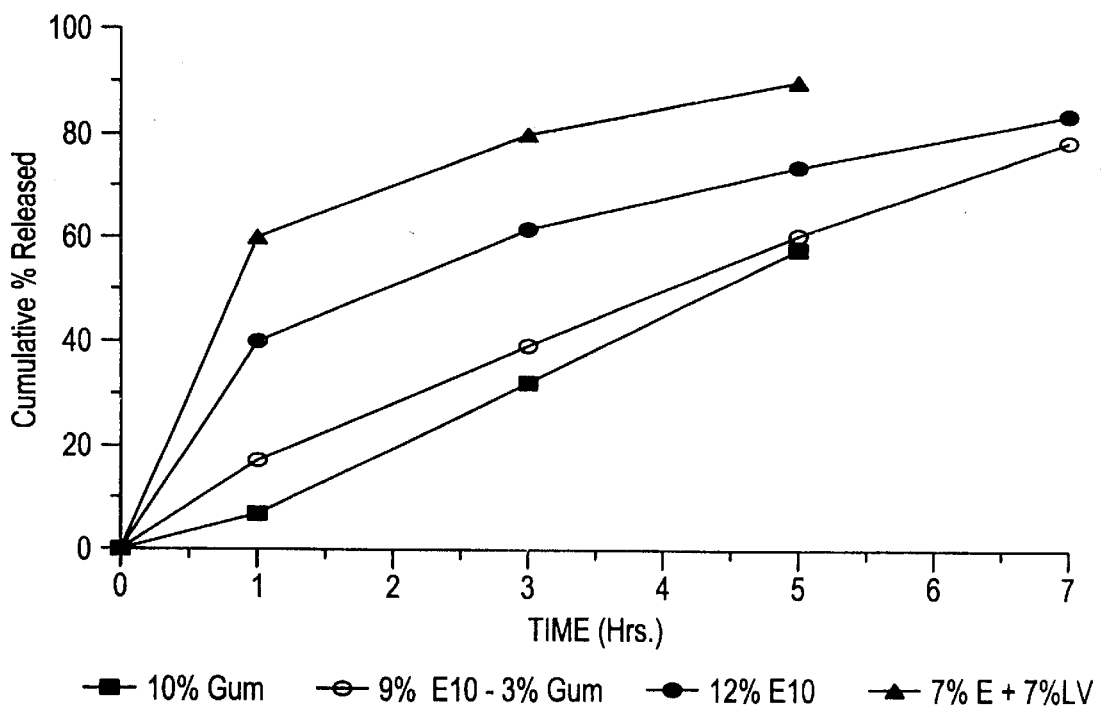
FIG. 4 shows a release profile of guaifenesin in water when the carrier is xanthan gum, two types of hydroxypropylmethyl cellulose and a synergistic effective amount of a combination of xanthan gum and hydroxypropylmethyl cellulose.

The release profiles were determined as in Example 3 and are shown in FIG. 4.

Again, as in the previous example, the drug release profile for the formulation containing the combination of hydroxypropylmethyl cellulose and xanthan gum was similar to the formulation containing xanthan gum alone. This is surprising since the formulation of the present invention contained mostly hydroxypropylmethyl cellulose. A small amount of Xanthan gum added to the HPMC improves the release profile significantly.

EXAMPLE 9 AND COMPARATIVE EXAMPLE 9

Tablets containing NIACIN were prepared by mixing the following ingredients or a V blender for 120 minutes.

|  | 17% K 15 M | 12% K 15 M + 1% Gum |
|---|---|---|
| Niacin | 500 | 500 |
| Methocel K15 | 110 | 84 |
| Xanthan Gum | 0 | 7 |
| Silicified MCC | 0 | 49.25 |
| Dicalcium Phosphate | 30 | 29.25 |
| Mg Stearate | 4 | 0 |
| Talc |  | 10.5 |
| Tablet weight | 634 | 700 |

Figure 5:
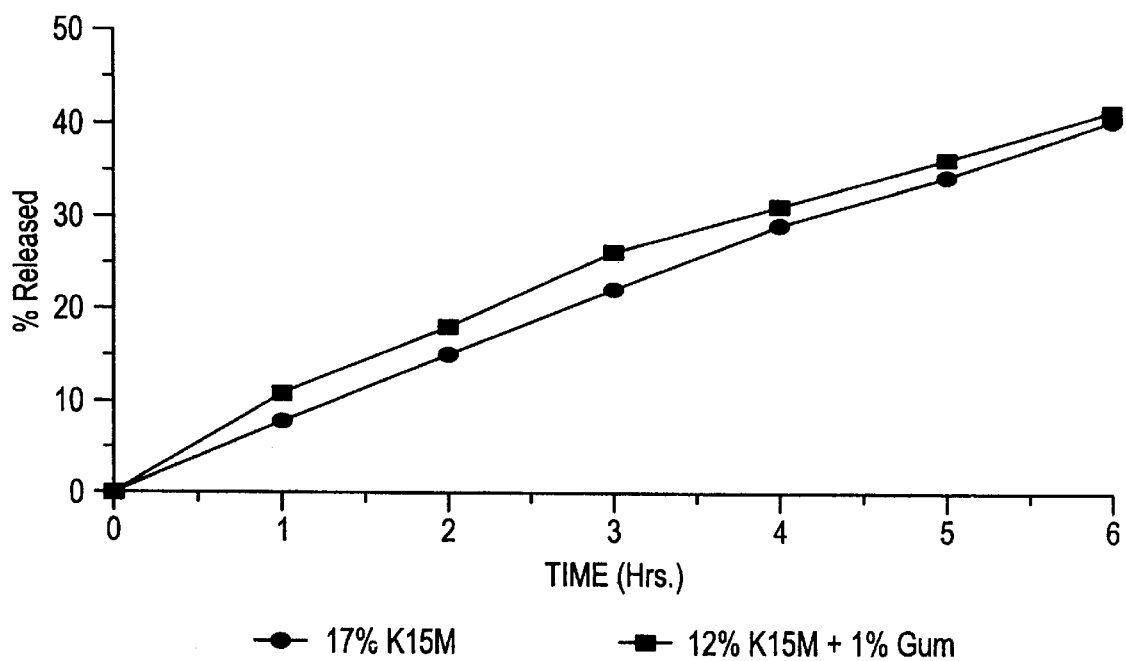
FIG. 5 shows a release profile of niacin in water when the carrier is hydroxypropylmethyl cellulose and a hydroxypropylmethyl cellulose and xanthan gum in synergistic effective amounts.

Each mixture was compressed into a tablet. Their release profiles were determined as described in Example 3 and are shown in FIG. 5. As clearly shown, the release profile of both were similar. However, the release profile of the present formulation was achieved using a smaller amount of HPMC. In fact, the amount of HPMC and xanthan gum utilized in the present formulation was less than the HPMC utilized in the comparative example.

EXAMPLE 10

Niacin (500 mg), Methocel K 15 M (90 mg), xanthan gum (7.5 mg) silicified microcrystalline cellulose (76.25 mg) and dicalcium phosphate (76.25 mg) were thoroughly mixed together in a blender for 120 minutes. The above mixture was compressed into a tablet. The release profile was determined as described in Example 3 and is tabulated hereinbelow.

| Time | % Release |
|---|---|
| 1 hour | 11.50 |
| 2 hour | 18.35 |
| 3 hour | 25.57 |
| 4 hour | 31.29 |
| 5 hour | 36.12 |
| 6 hour | 41.06 |

EXAMPLE 11

Niacin (500 mg), METHOCEL E10 M® (105 mg), xanthan gum (15 mg) and silicified microcrystalline cellulose (130 mg), and Talc (15 mg) were mixed together in a V blender for 120 minutes. The above mixture was compressed into a tablet. The release profile was determined as described in Example 3; it gave the following release profile.

| Time | % Release |
|---|---|
| 1 hour | 17.33 |
| 2 hour | 27.67 |

EXAMPLE 12

The procedure in Example 11 was repeated except that 37.5 mg of xanthan gum, and silicified microcrystalline cellulose (100 mg) were utilized instead of the amounts utilized therein. The release profile was determined as described in Example 3 and is tabulated hereinbelow:

| Time | % Release |
|---|---|
| 1 hour | 7.63 |
| 2 hour | 12.37 |
| 3 hour | 18.28 |
| 4 hour | 22.14 |
| 5 hour | 26.20 |
| 6 hour | 29.44 |

EXAMPLE 13

The procedure of Example 12 was repeated except that 30 mg of xanthan gum and 107.5 mg of silicified microcrystalline cellulose were used instead of the amounts utilized therein. The release profile was determined as in Example 3; it gave the following release profile.

| Time | % Release | |
|---|---|---|
| 1 hour | 8.46 | 8.85 |
| 2 hour | 13.32 | 11.28 |
| 3 hour | 16.56 | 16.93 |
| 4 hour | 23.61 | 20.24 |
| 5 hour | 27.95 | 24.91 |
| 6 hour | 31.51 | 28.88 |

EXAMPLE 14–33 AND COMPARATIVE EXAMPLE 11–12

Guaifenesin (600 mg) was mixed with 8 mg talc and METHOCEL®, xanthan gum and silicified microcrystalline cellulose in a V blender for 120 minutes. The various formulations are tabulated hereinbelow. As shown, the amount and type of METHOCEL varied, depending upon the formulation, wherein the amount of METHOCEL in each tablet varied from 32 mg (which corresponds to 4% by weight) to 64 mg (which corresponds to 8% by weight). Moreover, the amount of xanthan gum varied, ranging from 2.4 mg (corresponding to 0.3% by weight of the tablet to 24 mg (corresponding to 3% by weight of the tablet). The remainder was silicified microcrystalline cellulose, which was added in amounts to make a 800 mg tablet weight.

The mixture was tableted. The release profile for each was determined as described in Example 3 and each release profile is tabulated hereinbelow.

For comparative purposes, guaifenesin (600 mg) was mixed on a V blender for 120 minutes with 48 mg (% or 80 mg (10%) xanthan gum 7.5 mg and silicified microcrystalline cellulose to give a total weight of 800 mg. The mixture was compressed to give a tablet. The release profile was tested as above. The formulations as well as the release profile is depicted in the following table.

| | Polymer | Xanthan Gum | Release Profile | | | |
|---|---|---|---|---|---|---|
| | | | 1 hr | 3 hr | 5 hr | 7 hr |
| Comp. Ex. 11 | — | 10% | 6.43 | 31.14 | 56.37 | — |
| Comp. Ex. 12 | — | 6% | 10.58 | 57.68 | 97.52 | — |
| | HPMC K15M | | | | | |
| Example 14 | 7% | 2% | 14.16 | 33.72 | 58.08 | 76.40 |
| Example 15 | 7% | 1% | 20.42 | 42.97 | 61.59 | 77.30 |
| Example 16 | 6% | 0.5% | 26.69 | 53.83 | 72.47 | 90.89 |
| | HPMC E10M CR | | | | | |
| Example 18 | 9% | 3% | 15.6 | 37.6 | 59.01 | 77.90 |
| Example 19 | 7% | 1% | 29.24 | 54.8 | 70.86 | 89.42 |
| Example 20 | 6% | 1% | 13.66 | 41.91 | 65.41 | 86.70 |
| Example 21 | 8% | 0.6% | 21.89 | 48.90 | 67.12 | 87.15 |
| Example 22 | 7% | 1% | 21.43 | 46.65 | 69.65 | 83.88 |
| Example 23 | 7% | 0.5% | 22.40 | 49.88 | 69.05 | 85.98 |
| Example 24 | 5% | 0.5% | 21.85 | 49.59 | 74.48 | 90.59 |
| Example 25 | 5% | 0.3% | 40.85 | 70.22 | 88.20 | 95.11 |
| Example 26 | 5% | 0.4% | 49.61 | 76.70 | 91.24 | 97.12 |
| | HPMC E4M CR | | | | | |
| Example 27 | 8% | 1% | 22.99 | 50.19 | 71.68 | 88.58 |
| Example 28 | 6% | 0.5% | 38.30 | 65.20 | 82.69 | 92.94 |
| | HPMC E4M | | | | | |
| Example 29 | 8% | 1% | 18.02 | 42.05 | 63.34 | 77.89 |
| Example 30 | 6% | 0.5% | 45.80 | 68.86 | 85.32 | 95.76 |
| Example 31 | 6% | 1% | 21.39 | 51.35 | 74.94 | 91.29 |
| Example 32 | 6% | 0.7% | 29.34 | 59.08 | 79.83 | 92.88 |
| | HPMC E4M | | | | | |
| Example 33 | 6% | 0.6% | 42.82 | 74.08 | 92.0 | — |

EXAMPLE 34

Guaifenesin (600 mg), Methocel E10M (48 mg), xanthan gum (2.4 mg), microcrystalline cellulose (141.3 mg), Talc (8.00 mg) and coloring (0.3mg) are mixed for 120 minutes in a double cone blender. The mixture is compressed to form a 600 mg tablet.

EXAMPLE 35

Guaifenesin (400 mg), phenylpropanolamine HCl (75 mg), xanthan gum (38.8 mg), Methocel E10M, (62 mg), microcrystalline cellulose (133.34 mg), Talc (10.8 mg) and color (2 mg) are blended together and compressed into a tablet, as described in Example 34.

EXAMPLE 36

Guaifenesin (600 mg), pseudoephedrine HCl (120 mg), Methocel E10M (110 mg), xanthan gum (25 mg), microcrystalline cellulose (31.5 mg), Talc (13.5 mg) are blended together and compressed into a tablet (900 mg) as described in Example 34.

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the amended claims.

What is claimed is:

1. A solid sustained release pharmaceutical tablet for administering to a host, comprising a therapeutically effective amount of a pharmaceutically active ingredient, and a sustained release carrier therefor, said sustained release carrier comprising a synergistic combination of (a) a hydrocolloid selected from the group consisting of xanthan gum, guar gum, and alginic acid or pharmaceutically acceptable salt thereof, and (b) a cellulose ether to retard the release of the pharmaceutically active ingredient, said carrier being present in said formulation in less than about 40% by weight of the tablet, said hydrocolloid and cellulose ether being present in synergistic effective amounts to retard the release of said pharmaceutically active ingredient, said hydrocolloid being present in an amount ranging from about 0.3% to about 7.0% by weight of the tablet and said cellulose ether being present in an amount ranging from 3% to about 20% by weight of said tablet, whereby said cellulose ether is present in the carrier in an amount greater than 50% by weight of the carrier.

2. The tablet according to claim 1 in which the hydrocolloid is present in amounts less than about 5% by weight of the tablet.

3. The tablet according to claim 2 wherein the hydrocolloid is present in an amount less than about 1% by weight of the tablet.

4. The tablet according to claim 1 in which the sum of the amount of the hydrocolloid and the cellulose ether is less than about 25% by weight of the tablet.

5. The tablet according to claim 4 in which the sum of the amount of the hydrocolloid is less than about 20% by weight of the tablet.

6. The tablet according to claim 1 wherein the weight ratio of cellulose ether to hydrocolloid ranges from about 1:0.01 to about 1:0.4.

7. The tablet according to claim 6 wherein the weight ratio of cellulose ether to hydrocolloid ranges from about 1:0.05 to about 1:0.4.

8. The tablet according to claim 1 wherein the hydrocolloid is xanthan gum.

9. The tablet according to claim 1 wherein the cellulose ether is hydroxypropylmethyl cellulose.

10. The table according to claim 1 wherein an excipient is additionally present.

11. The tablet according to claim 1 wherein the cellulose ether is hydroxypropylmethyl cellulose and the hydrocolloid is xanthan gum.

12. The tablet according to claim 11 wherein the xanthan gum is present in amounts ranging from 0.1% to about 5% of the tablet.

13. The tablet according to claim 11 wherein the xanthan gum is present in amounts ranging from 0.3% to about 3% of the tablet.

14. The tablet according to claim 11 wherein the weight ratio of hydroxypropylmethyl cellulose to xanthan gum ranges from 1:0.01 to about 1:0.4.

15. The tablet according to claim 14 wherein the weight ratio of hydroxypropylmethyl cellulose to xanthan gum ranges from 1:0.05 to about 1:0.4.

16. The tablet according to claim 11 wherein the carrier comprises at most about 20% of the tablet.

17. The tablet according to claim 1 which additionally contains a lubricant in lubricating effective amounts.

18. A method of administering a pharmaceutically active agent or pharmaceutically acceptable salt thereof in a sustained release dosage form in tablet form, said method comprising administering to the patient a solid unit dose of a therapeutically effective amount of a pharmaceutically active ingredient and a sustained release carrier therefor, said sustained release carrier comprising a synergistic combination of (a) a hydrocolloid selected from the group consisting of xanthan gum, guar gum, and alginic acid or pharmaceutically acceptable salt thereof, and (b) a cellulose ether to retard the release of the pharmaceutically active ingredient, said hydrocolloid and cellulose ether being present in synergistic effective amounts to retard release of said pharmaceutically active ingredient, said carrier being present in less than about 40% by weight of the tablet, said hydrocolloid being present in an amount ranging from about 0.3% to about 7.0% by weight of the tablet and said cellulose ether being present in an amount ranging from about 3% to about 20% by weight of said tablet, whereby said cellulose ether is present in the carrier in an amount greater than 50% by weight.

19. The method of claim 18 wherein the hydrocolloid is present in an amount less than about 5% by weight.

20. The method of claim 19 wherein the hydrocolloid is present in an amount less than about 3% by weight.

21. The method of claim 18 wherein the hydrocolloid is xanthan gum.

22. The method of claim 18 wherein the cellulose ether is hydroxypropylmethyl cellulose.

23. The method of claim 18 or 22 wherein the ratio of cellulose ether to hydrocolloid ranges from 1:0.01 to about 1:0.4.

24. The method according to claim 18 wherein the tablet additionally contains a lubricating effective amount of a lubricant.

25. The tablet according to claim 1 wherein the cellulose ether is present in the carrier in an amount greater than about 60% by weight.

26. The tablet according to claim 25 wherein the cellulose ether is present in the carrier in an amount greater than about 66% by weight.

27. The tablet according to claim 26 wherein the cellulose ether is present in the carrier in an amount greater than about 75% by weight.

28. The tablet according to claim 11 wherein the hydroxypropylmethyl cellulose is present in the carrier in an amount greater than about 60% by weight.

29. The tablet according to claim 28 wherein the hydroxypropylmethyl cellulose is present in the carrier in an amount greater than 66% by weight.

30. The tablet according to claim 29 wherein the hydroxypropylmethyl cellulose is present in the carrier in an amount greater than about 75% by weight.

31. The method according to claim 18 where the cellulose ether is present in the carrier is an amount greater than about 60% by weight.

32. The method according to claim 31 wherein the cellulose ether is present in the carrier in an amount greater than about 66% by weight.

33. The method according to claim 32 wherein the cellulose ether is present in the carrier in an amount greater than about 75% by weight.

34. The method according to claim 18 wherein the hydrocolloid is xanthan gum and the cellulose ether is hydroxypropylmethyl cellulose.

35. The method according to claim 34 wherein the cellulose ether is present in the carrier in an amount greater than about 60% by weight.

36. The method according to claim 35 wherein the cellulose ether is present in the carrier in an amount greater than about 66% by weight.

37. The method according to claim 36 wherein the cellulose ether is present in the carrier in an amount greater than about 75% by weight.

38. In an improved method of retarding the release of a pharmaceutically active ingredient in a sustained release pharmaceutical composition in tablet form comprising said pharmaceutically active ingredient and a sustained release carrier comprising a cellulose ether, the improvement comprising incorporating homogenously into said carrier a hydrocolloid selected from the group consisting of xanthan gum, guar gum and alginic acid or pharmaceutically acceptable salts thereof, said hydrocolloid and said cellulose ether being present in an amount greater than 50% by weight of the carrier, said cellulose ether being present in an amount ranging from about 3% to about 20% by weight of the tablet and said hydrocolloid being present in an amount ranging from about 0.3% to about 7.0% weight of the tablet, and said hydrocolloid and cellulose ether being present in a synergic combination in synergistic effective amounts to retard the release of the pharmaceutically active ingredient whereby the rate of release of the pharmaceutically active ingredient from the pharmaceutical composition when the tablet is placed in an aqueous medium is slower relative to the rate of release of the pharmaceutically active ingredient in a tablet containing the same pharmaceutically active ingredient and said hydrocolloid in the same relative weight ratios but in the absence of cellulose ether or relative to a tablet containing the same pharmaceutically active ingredient and said cellulose ether in the same relative weight ratios but in the absence of said hydrocolloid.

39. The improved method according to claim 38 wherein the hydrocolloid is xanthan gum.

40. The improved method according to claim 38 wherein the cellulose ether is hydroxypropylmethyl cellulose.

41. The improved method according to claim 38 wherein the hydrocolloid is xanthan gum and the cellulose ether is hydroxypropylmethyl cellulose.

42. The improved method according to claim 38 or 41 wherein the cellulose ether is present in the carrier in an amount greater than about 60% by weight.

43. The improved method according to claim 42 wherein the cellulose ether is present in the carrier in an amount greater than about 66% by weight.

44. The improved method according to claim 43 wherein the cellulose ether is present in the carrier in amount greater than about 75% by weight.

45. The tablet according to claim 1 or claim 11 wherein the hydrocolloid is present in the carrier in an amount ranging from about 5% to about 40% by weight.

46. The method according to claim 18 or 34 wherein the hydrocolloid is present in the carrier in an amount ranging from about 5% to about 40% by weight.

47. The improved method according to claim 38 or 39 wherein the hydrocolloid is present in an amount ranging from about 5% to about 40% by weight.

* * * * *